(12) United States Patent
Pecor (10) Patent No.: US 6,287,326 B1
(45) Date of Patent: Sep. 11, 2001

(54) CATHETER WITH COILED MULTI-LUMEN HEAT TRANSFER EXTENSION

(75) Inventor: Robert Pecor, Aliso Viejo, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 09/366,640

(22) Filed: Aug. 2, 1999

(51) Int. Cl.[7] .................................................. A61F 7/00
(52) U.S. Cl. .......................... 607/105; 607/105; 604/113; 606/27
(58) Field of Search ............................ 607/96, 104, 105, 607/113; 606/27, 28, 20–23; 604/113

(56) References Cited

U.S. PATENT DOCUMENTS

| Re. 32,983 | 7/1989 | Levy ................... 428/36.92 |
| Re. 33,561 | 3/1991 | Levy ................... 428/36.92 |
| 2,058,780 | 10/1936 | Elliott ................... 128/401 |
| 2,077,453 | 4/1937 | Albright ................... 128/254 |
| 2,308,484 | 1/1943 | Auzin et al. ................... 18/58 |
| 3,125,096 | 3/1964 | Antiles et al. ................... 128/401 |
| 3,142,158 | 7/1964 | Podolsky ................... 62/3 |
| 3,238,944 | 3/1966 | Hirschhorn ................... 128/400 |
| 3,282,267 | 11/1966 | Eidus ................... 128/399 |
| 3,327,713 | 6/1967 | Eidus ................... 128/399 |
| 3,425,419 | 2/1969 | Dato ................... 128/400 |
| 3,504,674 | 4/1970 | Swenson et al. ................... 128/303.1 |
| 3,738,372 | 6/1973 | Shioshvili ................... 128/400 |
| 3,776,241 | 12/1973 | Magilton et al. ................... 128/400 |
| 3,897,790 | 8/1975 | Magilton et al. ................... 128/400 |
| 3,913,581 | 10/1975 | Ritson et al. ................... 128/303.1 |
| 4,010,795 | 3/1977 | Stenberg ................... 165/46 |
| 4,111,209 | 9/1978 | Wolvek et al. ................... 128/400 |
| 4,154,245 | 5/1979 | Daily ................... 128/400 |
| 4,249,923 | 2/1981 | Walda ................... 62/394 |
| 4,298,006 | 11/1981 | Parks ................... 128/399 |
| 4,416,280 | 11/1983 | Carpenter et al. ................... 128/399 |
| 4,416,281 | 11/1983 | Cooper et al. ................... 128/400 |
| 4,583,969 | 4/1986 | Mortensen ................... 604/49 |
| 4,672,962 | 6/1987 | Hershenson ................... 128/303.1 |
| 4,745,922 | 5/1988 | Taylor ................... 128/380 |
| 4,748,979 | 6/1988 | Hershenson ................... 128/303.1 |
| 4,750,493 | 6/1988 | Brader ................... 128/380 |

(List continued on next page.)

FOREIGN PATENT DOCUMENTS

| WO 98/26831 | 6/1998 | (WO) ........................... A61M/25/00 |
| WO 98/31312 | 7/1998 | (WO) ........................... A61F/7/12 |

Primary Examiner—Linda C. M. Dvorak
Assistant Examiner—Roy Gibson
(74) Attorney, Agent, or Firm—Burns Doane Swecker & Mathis LLP (57) ABSTRACT

A catheter includes a sealed multi-lumen heat transfer extension designed to internally circulate a coolant, and thereby cool tissue or fluid surrounding the catheter. The heat transfer extension includes a tube having a distally positioned region that coils about the tube's longitudinal axis. The tube houses multiple lumens running longitudinally along the tube. These lumens include one or more supply lumens and one or more return lumens. A distal fluid exchange reservoir resides at the tube's tip, for the purpose of redirecting fluid from the supply lumen(s) to the return lumen(s). The heat transfer extension may include a shape memory structure causing the heat transfer extension to vary its shape according to temperature. Namely, the extension assumes a coiled shape under predetermined shape-active temperatures, and it assumes a non-coiled shape under other predetermined shape-relaxed temperatures. The catheter also includes an interface having supply and return lines to provide coolant to the heat transfer extension, and remove coolant returning therefrom. To connect the supply/return lines with the supply/return lumens, the invention may include a fluid transfer housing. Optionally, one or more of the lumens may be configured as flow-through lumens to exchange fluids with the patient.

10 Claims, 9 Drawing Sheets

U.S. PATENT DOCUMENTS

| | | | |
|---|---|---|---|
| 4,754,752 | 7/1988 | Ginsberg et al. | 128/303.12 |
| 4,759,349 | 7/1988 | Betz et al. | 128/6 |
| 4,791,930 | 12/1988 | Suzuki et al. | |
| 4,813,210 | 3/1989 | Masuda et al. | 53/425 |
| 4,823,076 | 4/1989 | Haines et al. | 324/121 R |
| 4,844,074 | 7/1989 | Kurucz | 128/401 |
| 4,850,958 | 7/1989 | Berry et al. | 604/26 |
| 4,860,744 | 8/1989 | Johnson et al. | 128/303.1 |
| 4,883,455 | 11/1989 | Leonard | 604/4 |
| 4,899,741 | 2/1990 | Bentley et al. | 606/27 |
| 4,920,963 | 5/1990 | Brader | 128/402 |
| 4,941,475 | 7/1990 | Williams et al. | 128/692 |
| 4,987,896 | 1/1991 | Nakamatsu | 128/399 |
| 5,019,075 | 5/1991 | Spears et al. | 606/7 |
| 5,021,045 | 6/1991 | Buckberg et al. | 604/53 |
| 5,037,383 | 8/1991 | Vaslef et al. | 604/26 |
| 5,041,089 | 8/1991 | Mueller et al. | 604/96 |
| 5,066,578 | 11/1991 | Wikman-Coffelt | 435/1 |
| 5,078,713 | 1/1992 | Varney | 606/23 |
| 5,092,841 | 3/1992 | Spears | 604/96 |
| 5,098,376 | 3/1992 | Berry et al. | 604/26 |
| 5,106,360 | 4/1992 | Ishiwara et al. | 600/2 |
| 5,139,496 | 8/1992 | Hed | |
| 5,147,355 | 9/1992 | Friedman et al. | 606/23 |
| 5,147,385 | 9/1992 | Beck et al. | 623/1 |
| 5,151,100 | 9/1992 | Abele et al. | 606/28 |
| 5,158,534 | 10/1992 | Berry et al. | 604/4 |
| 5,174,285 | 12/1992 | Fontenot | 128/400 |
| 5,182,317 | 1/1993 | Winters et al. | 523/112 |
| 5,191,883 | 3/1993 | Lennox et al. | 128/401 |
| 5,195,962 * | 3/1993 | Martin et al. | 604/43 |
| 5,196,024 | 3/1993 | Barath | 606/159 |
| 5,211,631 | 5/1993 | Sheaff | 604/113 |
| 5,230,862 | 7/1993 | Berry et al. | 422/48 |
| 5,248,312 | 9/1993 | Langberg | 606/28 |
| 5,250,070 | 10/1993 | Parodi | 606/194 |
| 5,257,977 | 11/1993 | Eshel | 604/113 |
| 5,261,399 | 11/1993 | Klatz et al. | 607/104 |
| 5,262,451 | 11/1993 | Winters et al. | 523/112 |
| 5,269,758 | 12/1993 | Taheri | 604/96 |
| 5,275,595 | 1/1994 | Dobak, III | 606/23 |
| 5,279,598 | 1/1994 | Sheaff | 604/290 |
| 5,281,213 | 1/1994 | Milder et al. | 606/15 |
| 5,281,215 | 1/1994 | Milder | 606/20 |
| 5,324,286 | 6/1994 | Fowle | 606/23 |
| 5,338,770 | 8/1994 | Winters et al. | 523/112 |
| 5,342,301 | 8/1994 | Saab | 604/96 |
| 5,342,693 | 8/1994 | Winters et al. | 428/447 |
| 5,354,277 | 10/1994 | Guzman et al. | 604/113 |
| 5,411,477 | 5/1995 | Saab | 604/96 |
| 5,423,807 | 6/1995 | Milder | 606/20 |
| 5,437,673 | 8/1995 | Baust et al. | 606/23 |
| 5,452,582 | 9/1995 | Longsworth | 62/51.2 |
| 5,478,309 | 12/1995 | Sweezer et al. | 604/4 |
| 5,486,204 | 1/1996 | Clifton | 607/96 |
| 5,486,208 | 1/1996 | Ginsburg | |
| 5,531,776 | 7/1996 | Ward et al. | 607/105 |
| 5,545,161 | 8/1996 | Imran | 606/41 |
| 5,562,606 | 10/1996 | Huybregts | 604/8 |
| 5,609,620 | 3/1997 | Daily | 607/105 |
| 5,624,392 | 4/1997 | Saab | 604/43 |
| 5,655,548 | 8/1997 | Nelson et al. | 128/898 |
| 5,656,420 | 8/1997 | Chien | 435/1.2 |
| 5,693,080 | 12/1997 | Wallstén et al. | 607/105 |
| 5,702,435 | 12/1997 | Maytal | 607/104 |
| 5,716,386 | 2/1998 | Ward et al. | 607/106 |
| 5,733,319 | 3/1998 | Neilson et al. | 607/105 |
| 5,735,809 | 4/1998 | Gorsuch | 604/4 |
| 5,758,505 | 6/1998 | Dobak, III et al. | 62/6 |
| 5,759,182 | 6/1998 | Varney et al. | 606/21 |
| 5,787,715 | 8/1998 | Dobak, III et al. | 62/51.2 |
| 5,837,003 | 11/1998 | Ginsburg | 607/106 |
| 5,899,899 | 5/1999 | Arless et al. | |
| 5,957,963 * | 9/1999 | Dobak, III | 607/104 |
| 5,976,152 * | 11/1999 | Regan et al. | 606/108 |
| 6,033,383 * | 3/2000 | Ginsburg | 604/113 |
| 6,093,199 * | 7/2000 | Brown et al. | 606/200 |
| 6,120,483 * | 9/2000 | Davey et al. | 604/247 |

* cited by examiner

CATHETER WITH COILED MULTI-LUMEN HEAT TRANSFER EXTENSION

BACKGROUND OF THE INVENTION

1. Field of the Invention

The present invention concerns a catheter that effects heat transfer using a coiled hollow tube at the catheter's distal end.

2. Description of the Related Art

In warm blooded creatures, temperature regulation is one of the most important functions of the body. Despite the known importance of properly maintaining body temperature, scientists have discovered certain beneficial effects of artificially inducing a hypothermic state. For instance, cooling the body can help regulate vital functions during surgery by lowering the metabolism. With stroke, trauma, and other conditions, hypothermia is believed to reduce the permeability of the blood/brain barrier. Also, induced hypothermia is believed to inhibit the release of damaging neurotransmitters, inhibit calcium mediated effects, inhibit brain edema, and lower intra cranial pressure. Regardless of the particular mechanism, the present invention understands that fevers degrade the outcomes for patients suffering from brain trauma or stroke, and moreover that hypothermia improves the outcomes for such patients.

Hypothermia may be induced locally or systemically. With local hypothermia, physicians focus their cooling efforts on a particular organ, limb, anatomical system, or other region of the body. With systemic hypothermia, body temperature is lowered without particular attention to any body part.

Under one technique for inducing systemic hypothermia, physicians cool the patient's entire body by packing it in ice. Although this technique has been used with some success, some physicians may find it cumbersome, and particularly time consuming. Also, it is difficult to precisely control body temperature with ice packing. As a result, the patient's body temperature overshoots and undershoots the optimal temperature, requiring physicians to add or remove ice. Furthermore, there is some danger of injuring the skin, which is necessarily cooled more than any other body part.

In another approach to systemic hypothermia, the patient is covered with a cooling blanket, such as an inflatable air-or water-filled cushion. Physicians control the patient's temperature by regulating the temperature of the inflation medium. Nonetheless, some delay is still inherent, first for a cooling element to change the temperature of the cooling medium, and then for the temperature adjusted cooling medium to cool the desired body part. This delay is even longer if the targeted body part is an internal organ, since the most effective cooling is only applied to the skin, and takes some time to successively cool deeper and deeper layers within the body.

The present invention recognizes that a better approach to inducing hypothermia is by circulating a cooling fluid through a cooling catheter placed inside a patient's body. The catheter may be inserted into veins, arteries, cavities, or other internal regions of the body. The present assignee has pioneered a number of different cooling catheters and techniques in this area. Several different examples are shown in U.S. application Ser. No. 09/133,813, entitled "Indwelling Heat Exchange Catheter and Method of Using Same," filed on Aug. 13, 1998. Further examples are illustrated in U.S. application Ser. No. 09/294,080 entitled "Catheter With Multiple Heating/Cooling Fibers Employing Fiber Spreading Features," filed on Apr. 19, 1999 in the names of Blair D. Walker et al. The foregoing applications are hereby incorporated into the present application by reference. These applications depict many catheters, including some where the tip region includes multiple hollow fibers. The fibers carry a coolant that is circulated through the catheter. The thin walls and substantial surface area of the fibers efficiently transfer heat from surrounding body fluids/tissue to the coolant, thereby cooling the patient.

Advantageously, cooling catheters are convenient to use, and enable doctors to accurately control the temperature of a targeted region. The present invention provides one such catheter.

SUMMARY OF THE INVENTION

Broadly, the present invention concerns a catheter with a sealed multi-lumen heat transfer extension designed to internally circulate a coolant, and thereby cool tissue or fluid surrounding the catheter. The heat transfer extension comprises a tube having a distally positioned region that forms a coil about the tube's longitudinal axis. This tube has multiple lumens that longitudinally span the tube, including one or more supply lumens and one or more return lumens. In one arrangement, the lumens include a centrally disposed return lumen surrounded by a number of parallel supply lumens, where the supply lumens are cross-sectionally arranged in a circle around the return lumen. A distal fluid exchange reservoir resides at the tube's tip, for the purpose of redirecting fluid from the supply lumens to the return lumen. In one embodiment, the heat transfer extension is permanently shaped to provide the desired coil shape. In a different embodiment, heat transfer extension may include shape memory structure causing the heat transfer extension to vary its shape according to temperature. Namely, the tube assumes a coiled shape under predetermined shape-active temperatures, and it assumes a flexible shape under other predetermined shape-relaxed temperatures. As examples, the shape memory structure may comprise a shaping wire longitudinally running through the extension, or shape memory material built into the extension. The catheter also includes supply and return lines to provide coolant to the heat transfer extension, and remove coolant returning therefrom. To interface the supply/return lines with the supply/return lumens, the invention may employ a fluid transfer housing.

Accordingly, in one embodiment, the invention may be implemented to provide an apparatus such as a catheter with a multi-lumen heat transfer extension having a distal region that has a coiled shape under some or all conditions. In another embodiment, the invention may be implemented to provide methods of manufacturing or utilizing such a catheter.

The invention affords its users with a number of distinct advantages. First, the invention provides significant heat exchange because of the heat transfer extension's substantial surface area. Due to the coiled configuration of the heat transfer extension, the catheter includes a substantial surface area that easily fits into a small region inside the patient. Additionally, the catheter of this invention minimizes the creation of blood clots. This is because the catheter provides a single heat transfer extension free from any junctions, constrictions, or abutting components that might otherwise encourage blood clots. As another advantage, owing to the unitary design of the heat transfer extension, the catheter of this invention is more easily manufactured than more complicated designs. The invention also provides a number of

DETAILED DESCRIPTION

The nature, objectives, and advantages of the invention will become more apparent to those skilled in the art after considering the following detailed description in connection with the accompanying drawings.

Hardware Components & Interconnections
Introduction

Broadly, this invention concerns a catheter with a sealed multi-lumen heat transfer extension designed to internally circulate a coolant, and thereby cool tissue or fluid surrounding the catheter. The elongated heat transfer extension contains multiple lumens longitudinally spanning the heat transfer extension. In an exemplary embodiment, these lumens include a central lumen surrounded by multiple peripheral lumens. In this embodiment, the central lumen constitutes a supply lumen, whereas the peripheral lumens constitute return lumens (or vice-versa). A distal fluid exchange reservoir provides a fluid redirecting path between the central lumen and the peripheral lumens.

The catheter has largely coextensive coolant supply and return lines, connected at a distal end to the coiled multi-turn heat transfer extension. The heat transfer extension is coupled to the supply/return lines by a fluid transfer housing. The fluid transfer housing forms a sealed fluid path between the return lumen and the return line, and also forms a sealed fluid path between the supply lumens and the supply line.

A cooling fluid ("coolant") travels longitudinally out and back through a sealed path inside the catheter, without contacting the tissue or body fluid surrounding the catheter. This catheter directs coolant down the supply line and supply lumens to the catheter's tip, where the coolant reverses direction in the fluid exchange reservoir. Returning fluid progresses from the fluid exchange reservoir through the return lumen, and then the return line.

The coolant comprises a fluid having suitable properties of heat transfer, bio-compatibility, viscosity, etc. The coolant may be a liquid or gas, with saline being one example. As an alternative to coolant, a suitable heating fluid may be used to induce hyperthermia rather that hypothermia.

More Detailed Explanation of Structure

Figure 1:
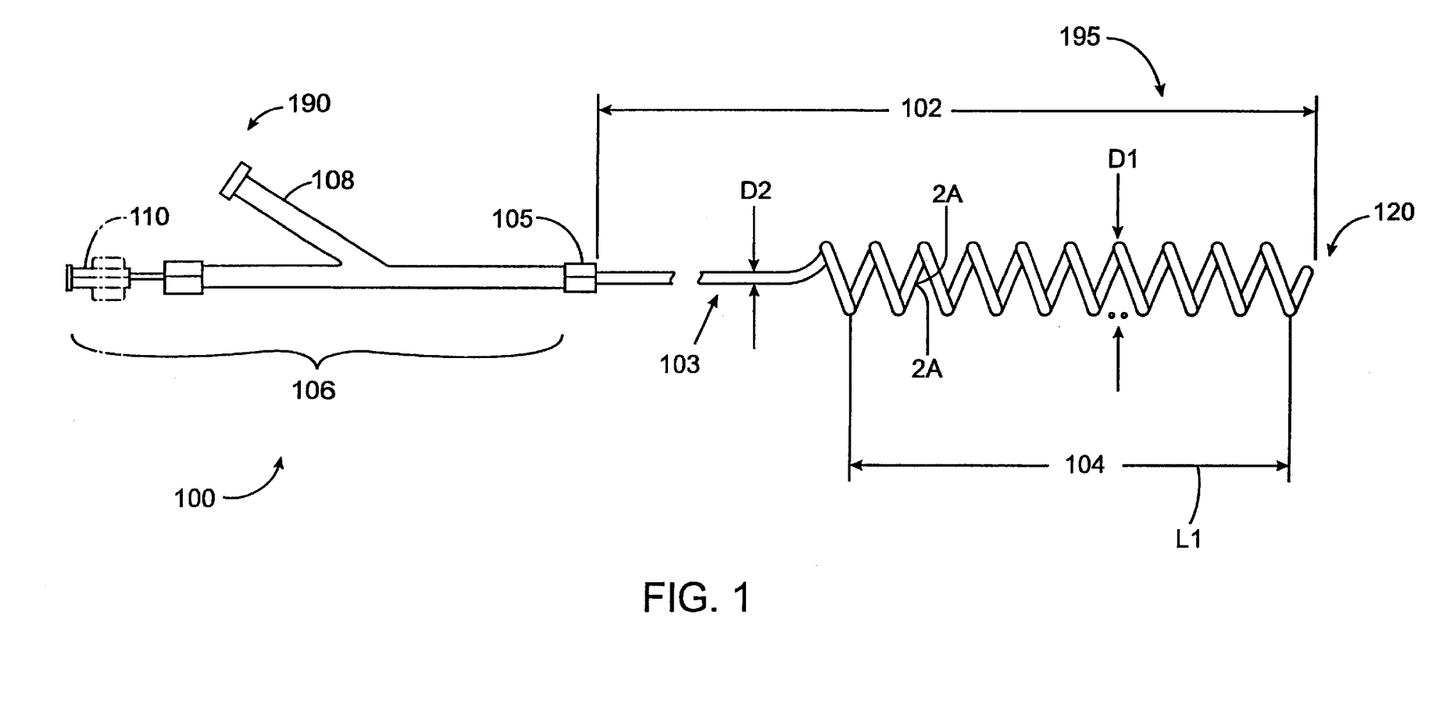
FIG. 1 is a plan view of the hardware components and interconnections of a catheter with a coiled, multi-lumen heat transfer extension, in accordance with the invention.

FIG. 1 shows a catheter 100 that exemplifies this invention. The catheter 100 includes an elongated coiled multi-turn heat transfer extension 102, a fluid transfer housing 105, and a pump interface 106. For ease of explanation, the catheter 100 and its subcomponents are discussed in terms of a proximal end 190 (or direction) and a distal end 195 (or direction).

The heat transfer extension 102 is a sealed construct that internally circulates a coolant, and thereby cools adjacent bodily tissue or fluid surrounding the catheter. The heat transfer extension 102 comprises a suitably flexible and nonallergenic material with consistent mechanical performance over a range of expected temperatures such as 0–40° Celsius. Some exemplary materials include poly ether amide block copolymers, polyurethane, polyethylene, poly vinyl chloride, and the like. The heat transfer extension 102 comprises a tube-shaped member that includes a coiled region 104 and a straight region 103. At a distal tip 120, the extension 102 includes a distal fluid reservoir (described below), which may be referred to as a "plenum." This fluid reservoir provides a fluid redirecting path between the supply lumens and the return lumen.

For use in the inferior vena cava, the extension 102 may have an overall length of about 100 centimeters when straight (about 50 centimeters when coiled). The coiled region 104 has a length "$L_1$" of about 15 centimeters when configured into repeating coils, where each coil has a diameter "$D_1$" of about two centimeters. When pulled straight, the coiled region 104 would have a length of about 65 centimeters. The tube-shaped member that constitutes the heat transfer extension 102 may have a diameter "$D_1$" of about 0.04 centimeters. Ordinarily skilled artisans (having the benefit of this application) should understand that the different relative lengths of coiled and straight regions 104, 103 may be used, with one possibility even being elimination of any straight region whatsoever.

The extension 102 is coupled to the pump interface 106 by the fluid transfer housing 105. Alternatively, the fluid transfer housing 105 may be omitted from the invention, with the heat transfer extension 102 being coupled directly to the interface 106. The pump interface 106 provides a means for supplying coolant to the extension 102 and receiving a return flow of coolant therefrom. As an example, the pump interface 106 may comprise a "Y" connector, as described in the parent application identified above. The interface 106 includes a coolant supply connector 108 and a coolant return connector 110, each coupled to respective lines (not shown) running internally along the length of the interface 106. The connector 110 may comprise a well known Luer port, for example.

Internally, the extension 102 includes one or more supply lumens, and one or more return lumens. Cooperatively, the supply/return lumens carry fluid out to the extension's distal tip and back. The housing 105 couples the return lumen(s) to the lines leading to the coolant return connector 110, and the supply lumen(s) to the lines leading to the coolant supply connector 108.

Figure 2A:
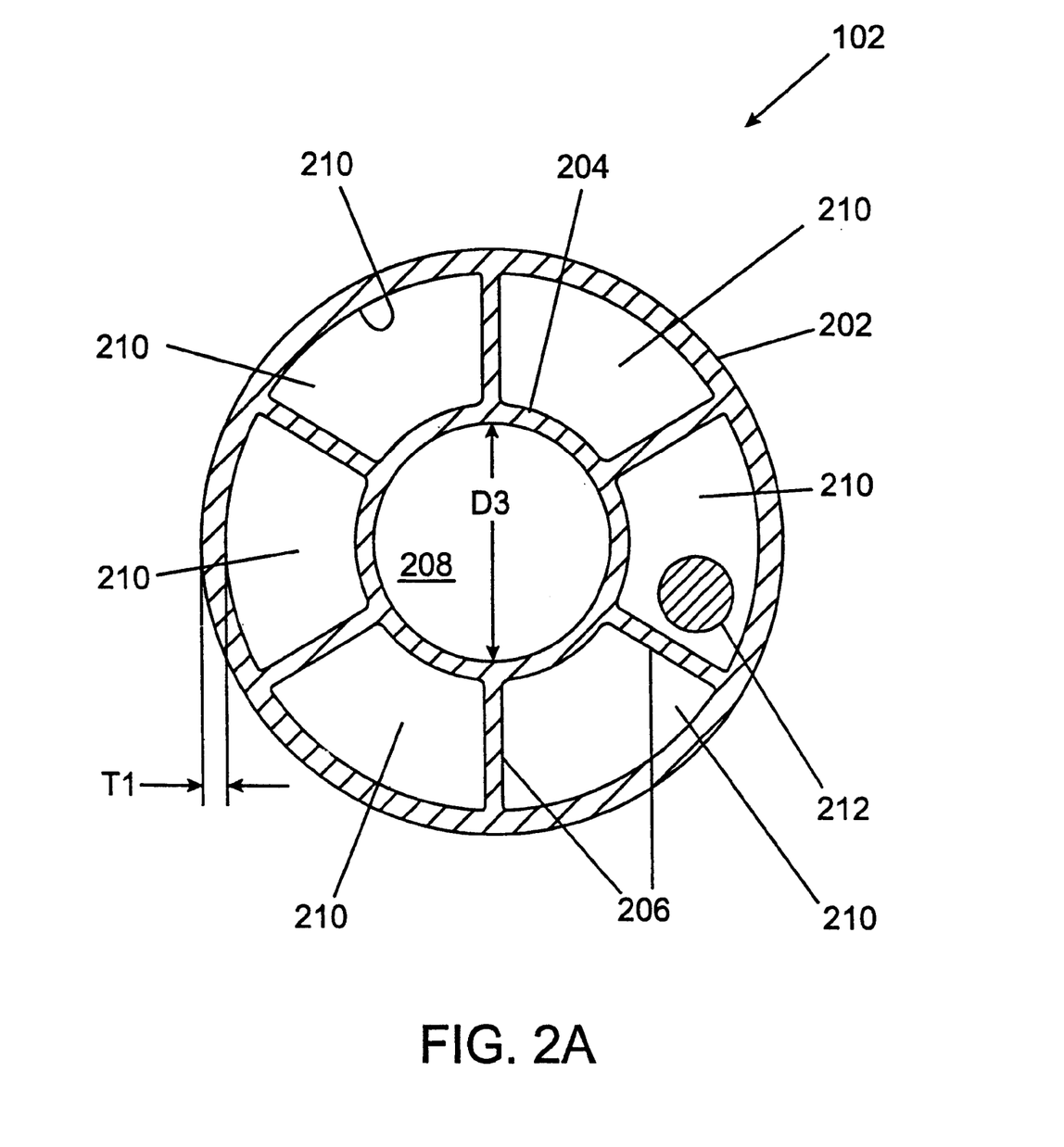
FIG. 2A is a cross-sectional view of the heat transfer extension of the catheter of FIG. 1 taken across the line 2A—2A, in accordance with the invention.

FIG. 2A shows one exemplary construction of the heat transfer extension 102. In this example, the extension 102 includes a single return lumen 208 central to the tube, and several supply lumens peripherally located around the return lumen. The extension 102 includes an outer wall 202 and a concentric inner wall 204. A number of ribs 206 hold the walls 202, 204 a fixed distance apart, and prevent the outer wall 202 from collapsing. The inner wall 204 defines a central longitudinal lumen 208, and the walls 202, 204 and ribs 206 cooperatively define multiple longitudinal peripheral lumens 210. The peripheral lumens 210 are also referred to as "supply" lumens, because they are used to carry coolant outward to the catheter's distal tip; in contrast, the central lumen 208 may be referred to as a "return lumen" because it carries coolant returning to the interface 106 from the heat transfer extension's distal tip. Relatedly, the housing 105 couples the return lumen to the coolant return connector 110, and the supply lumens to the coolant supply connector 108, as discussed in more detail below.

The invention contemplates various structure for providing heat transfer extension 102 with its coiled shape. In one embodiment, the heat transfer extension 102 is permanently coiled by heat treating or another process. In another embodiment, represented in FIG. 2A, the heat transfer extension 102 additionally includes a shaping wire 212 that runs longitudinally along the length of the tube 102 within one of the peripheral lumens 210. The shaping wire 212 comprises a shape memory substance causing the wire to assume a coiled shape under certain "shape-active" temperatures and a non-coiled shape under other "shape-relaxed" temperatures. The introduction of shape memory into the shaping wire 212 is discussed in greater detail below, along with other manufacturing operations. As a specific example, the wire may comprise a material such as nickel-titanium (e.g., Nitinol) with a diameter of about 0.05 millimeters. In a different embodiment, the shaping wire 212 may be omitted, with shape memory being introduced directly (i.e., built-in to) into the heat transfer extension material itself. For this purpose, shape memory polymeric materials such as specialized polyurethane may be used. As a further embodiment, the shaping wire 212 may be used along with some built-in shape memory incorporated into the tube material, albeit a lesser amount than necessary without the shaping wire 212.

Preferably, the dimensions of the lumens are chosen to balance fluid flow resistance in the return lumen 208 against collective fluid flow in the supply lumens 210, thereby minimizing the overall resistance of fluid traversing the extension 102. In the illustrated example, there are six ribs 206. According to one exemplary implementation, the extension 102 may have an overall diameter ("$D_2$," FIG. 1) of about 0.4 centimeters, with the walls 202, 204 and the ribs 206 each having a thickness ("$T_1$," FIG. 2A) of about 0.18 millimeters. In this example, the central lumen 208 has an inner diameter ("$D_3$," FIG. 2A) of about 1.6 millimeters.

Figure 2B:
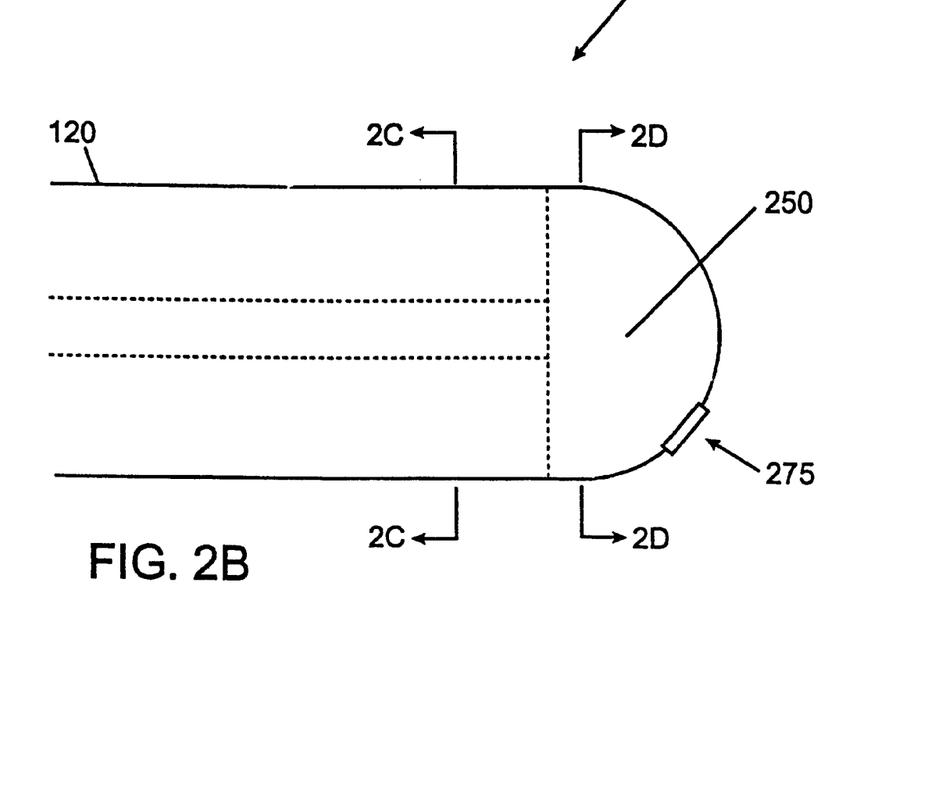
FIG. 2B is a plan view of the catheter of FIG. 1 showing the distal tip in greater detail, with portions shown in phantom, according to the invention.
Figure 2C:
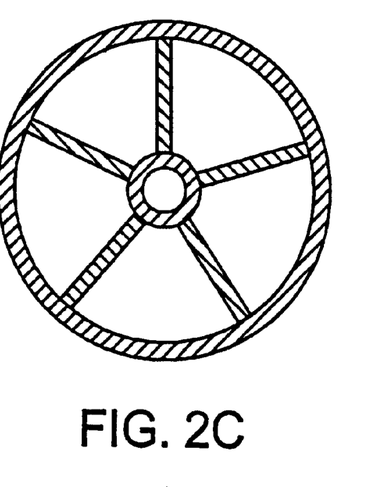
FIGS. 2C–2D are cross-sectional views of the catheter of FIG. 2B, according to the invention.
Figure 2D:
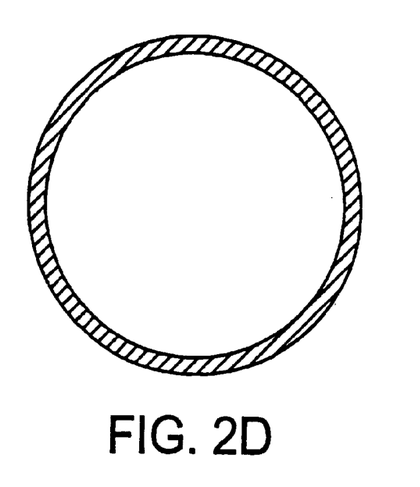

FIG. 2B shows the extension's distal tip 120 in greater detail. As mentioned above, the distal tip 120 of the extension 102 includes a distal fluid reservoir, also referred to as a "plenum." The fluid reservoir is shown by 250, and comprises a region where some or all of the ribs and central lumen are absent, thereby providing a common area where fluid is received from open ends of the supply lumens, and redirected into the open end of the return lumen. FIG. 2C shows the lumens proximally of the reservoir 250 in cross-section, whereas FIG. 2D shows the open region of the fluid reservoir 250 in cross-section.

Figure 2E:
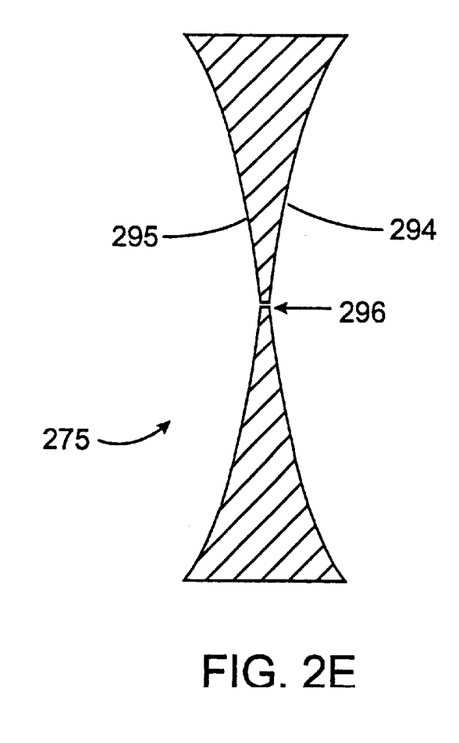
FIG. 2E is a cross-sectional diagram of a valve for use in "over the wire" applications, according to the invention.
Figure 2F:
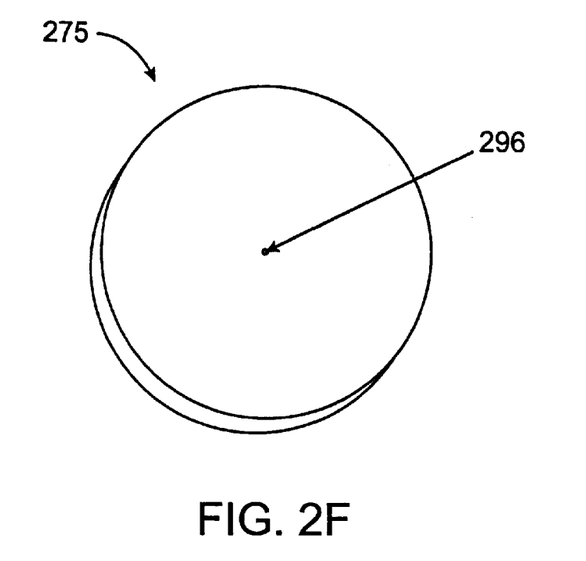
FIG. 2F is a perspective view of the valve of FIG. 2E, according to the invention.

The catheter of this invention may be used in "over the wire" applications, where a straight, rigid guide wire (not shown) is inserted into the body, and then the catheter is slid over the wire into place. For "over the wire" use, the catheter's distal tip may include a pass-through valve 275 to selectively admit a guide wire or "mandrel" in the direction toward the proximal end of the extension 102. This valve 275 also re-seals itself when the guide wire is removed in the opposite direction. In one embodiment, the valve 275 may comprise a disk-shaped member as shown in FIGS. 2E and 2F. This disk has opposing concave sides 294–295 and a tiny, central aperture 296. As the guide wire (not shown) passes through the aperture 296, it temporarily enlarges the aperture 296. However, due to the softness and elasticity of the valve 275, the valve 275 returns to its original state when the guide wire is removed. Accordingly, the valve 275 is made from material of suitable elasticity, hardness, biocompatibility, and other properties to suit these purposes. Some exemplary materials include silicon or plastics. Alternatively, the valve 275 may comprise an aperture with one or more normally seated (and sealed) flaps, a spongy membrane, a mechanical device, or another suitably penetrable but resealable member. As discussed below, in "over the wire" applications the catheter is positioned in a patient's body by sliding the catheter over the guide wire, such that the guide wire passes into one of the lumens. This valve 275 may be omitted in catheters that will not be used in "over the wire" applications.

Figures 3A, 3B, 3C, 3D:
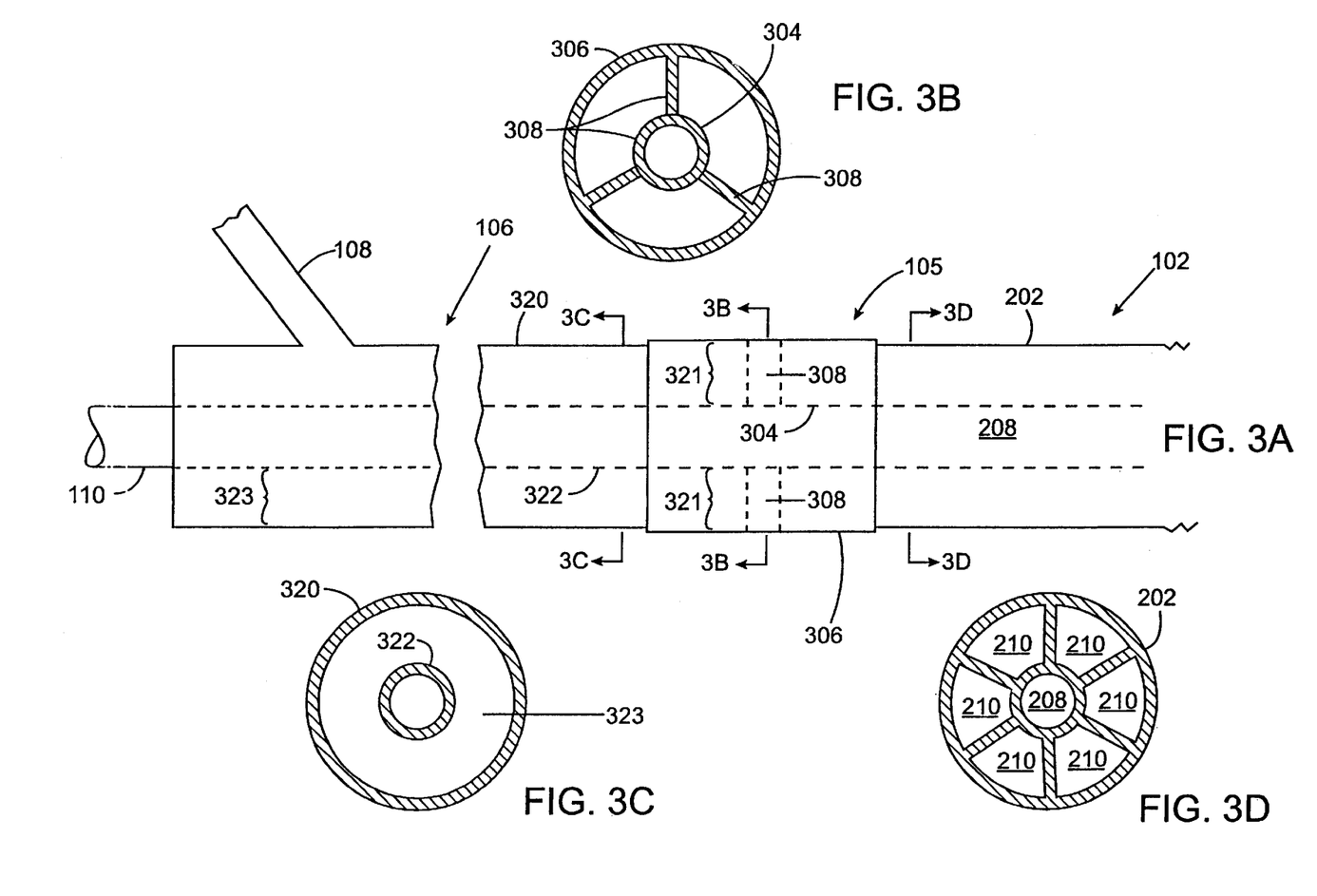
FIG. 3A is a plan view of the catheter of FIG. 1 illustrating fluid flow paths of the invention in greater detail.
FIGS. 3B–3D are different cross-sectional diagrams of the catheter of FIG. 3A, according to the invention.

Reference is now made to FIG. 3A to explain how the components of the heat transfer extension 102 (as shown in FIG. 2A) connect to the pump interface 106. Namely, FIG. 3A provides a detailed diagram of the fluid flow paths between heat transfer extension lumens, the fluid transfer housing 105, and the pump interface 106. Generally, the fluid transfer housing 105 couples the extension 102 to the pump interface 106, and includes an outer casing 306 and a transfer pipe 304. At one end, the casing 306 is sealed to the outer wall 202 of the extension 102; at the opposite end, the casing 306 is sealed to an outer wall 320 of the pump interface 106.

As shown in FIG. 3B, the pipe 304 is held in place by various ribs 308. In this example, there are three ribs 308 that extend from the pipe 304 at 120° angles. The ribs 308 keep the pipe 304 in a sufficiently central position to align it with the central lumen 208. As shown, the ribs 304 do not extend the full length of the housing 105 (from end to end), although they may do so if desired. At one end, the pipe 304 is sealed to the central lumen 208, which is shown in FIG. 3D. At the opposite end, the pipe 304 is sealed to a return line 322 of the pump interface 106, shown in FIGS. 3A and 3C. The return line 322 of the pump interface 106 ultimately connects to the return connector 110.

The housing 105 facilitates fluid flow between the central lumen 208 and the return connector 110 using the pipe 304. In the opposite direction, a passageway 321 (FIG. 3A) between the casing 306 and the pipe 304 permits fluid flow between the coolant supply connector 108 and the supply lumens 210. Namely, fluid flows from the supply connector 108 into a passageway 323 between the return line 322 and the outer wall 320 (FIGS. 3A, 3C), then into the passageway 321 between the casing 306 and pipe 304, and finally into the supply lumens 210 (FIG. 3D). The passageway 323 between the return line 322 and outer wall 320 may be referred to as a "supply line."

Figures 3E, 3F, 3G, 3H:
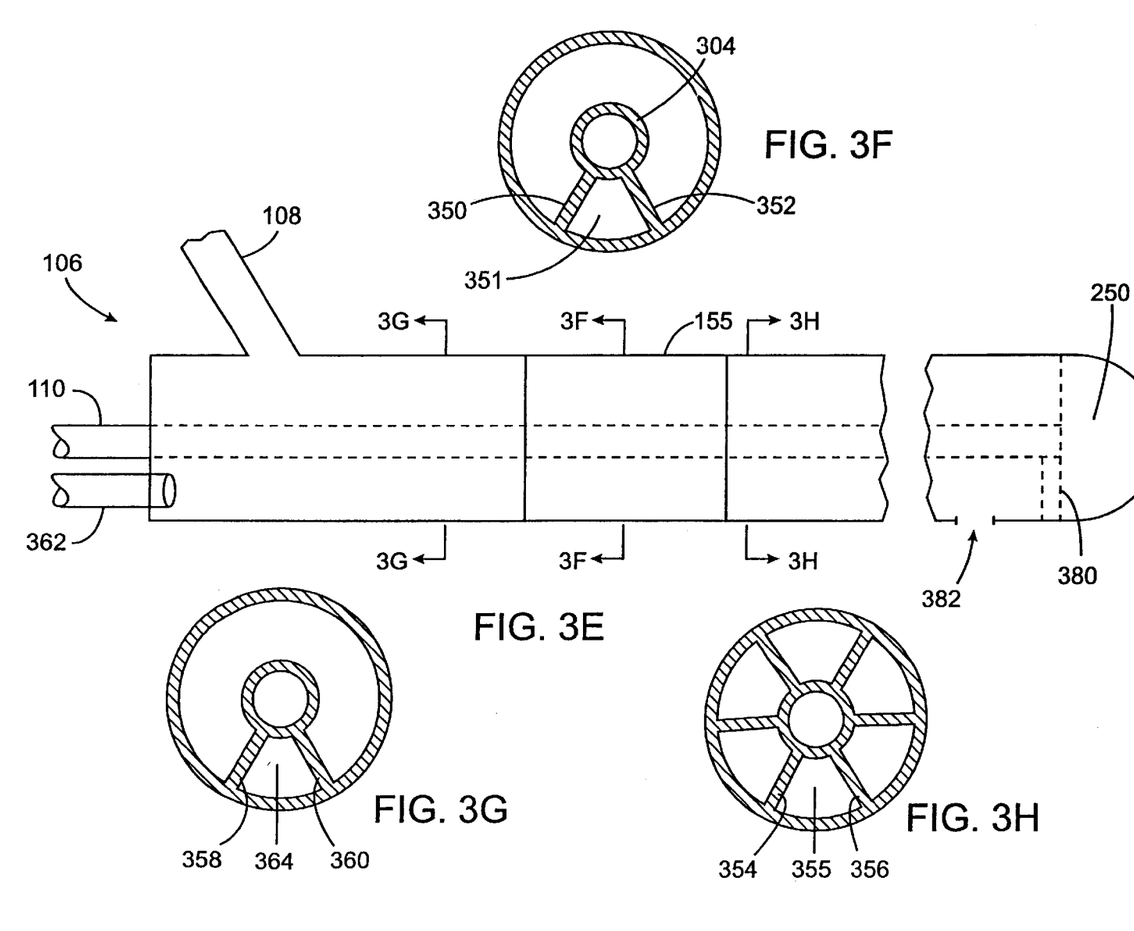
FIG. 3E is a plan view of the catheter of FIG. 3A illustrating an alternative embodiment capable of exchanging fluid with the patient, in accordance with the invention.
FIGS. 3F–3H are different cross-sectional diagrams of the catheter of FIG. 3E, according to the invention.

FIGS. 3E–3H illustrate another embodiment, where one lumen is specially configured to deliver or receive fluid to/from the patient during while the catheter is deployed. This lumen may be referred to as a flow-through lumen. In FIG. 3E, the flow-through lumen is provided by dedicating one of the (peripherally located) supply lumens, as shown by 355 (FIG. 3H).

In contrast to the usual lumens that open into the fluid reservoir at the catheter's tip, the flow-through lumen 355 meets a barrier 380 (FIG. 3E) that prevents fluid from the lumen 355 from mixing in the reservoir 250. Instead, the flow-through lumen 355 is provided with an opening 382 (FIG. 3E) enabling fluid to flow into and/or out of the distal end of the lumen 355. At the flow-through lumen's proximal end, the fluid transfer housing 155 includes ribs 350, 352 (FIG. 3F) that define a flow-through passageway 351 that exactly matches and seals to the flow-through lumen 355. Advantageously, the fluid transfer housing 105 in this embodiment may omit the ribs 308 of FIG. 3A, since the pipe 304 is now held in place by the ribs 350, 352 required to define the flow-through passageway 351. As shown in FIG. 3G, the sealed flow path defined by the flow-through lumen 355 and passageway 351 continues inside the pump interface 106 by virtue of ribs 358, 360 located therein, these ribs defining a flow-through passageway 364. The passageway 364 vents to a flow-through port 362 (FIG. 3E).

In use, the flow-through lumen 355 is not used for cooling, since it is disconnected from the coolant circulation path. Instead, the flow-through lumen 355 may be employed for the purpose of delivering materials (such as medicine) to the patient, sampling materials (such as blood) from the patient, etc. For example, to deliver medicine to the patient, the medicine is first introduced into the port 362. The medicine flows through the passageway 364, the passageway 351, the flow-through lumen 355, and finally exits the heat transfer extension 102 through the opening 382 into the patient's blood, other fluid/tissue that immerses the catheter.

Although not illustrated, more than one of the lumens may be configured as flow-through lumens, being sure to leave at least one supply and one return lumen to form a continuous coolant flow path. In this way, various concurrent operations can be performed, such as concurrently sampling and delivery, delivering different medicines simultaneously, etc.

To further enhance the operation of the catheter 100, several additional features may be provided. First, the catheter 100 may be manufactured with one or more radiopaque markers, to assist physicians in positioning the catheter 100 with x-rays. As one option, distal and proximal regions may be separately marked to easily identify the outer dimensions of the heat transfer extension 102. To further enhance the catheter's radioactive signature, the entire catheter 102 may incorporate a radiopaque material of contrasting intensity with the distal/proximal markers. An example of one radiopaque substance is Barium Sulfate. As another feature, a coating of heparin or another anti-clotting agent may be applied to outer portions of the tube 102 or any other regions with exposure to a patient's blood. This helps discourage clotting of blood surrounding the catheter 100 during use.

Operation

In addition to the various hardware embodiments described above, the invention also includes different method aspects, such as techniques for manufacturing and using such catheters.

Manufacturing this Catheter

Figure 4:
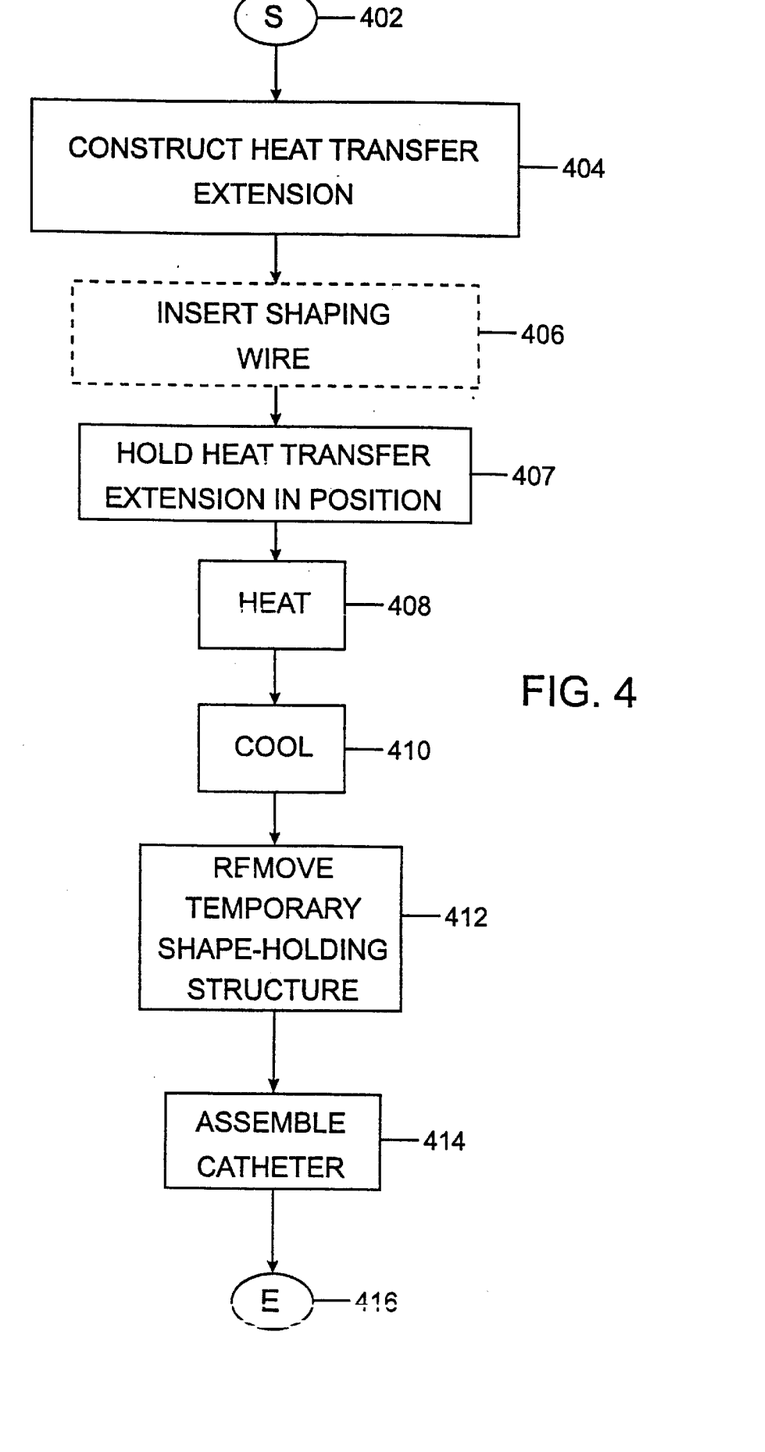
FIG. 4 is a flowchart of an operational sequence for manufacturing the catheter of FIG. 1 in accordance with the invention.

FIG. 4 shows a sequence 400 of exemplary operations for constructing one example of the various embodiments of catheter of this invention. For ease of explanation, but without any intended limitation, the example of FIG. 4 is described in the specific context of the catheter 100 (FIG. 1) described above. Step 402 marks the beginning of the sequence 400. In step 404, technicians construct the heat transfer extension 102. The extension 102, including the tube, walls, and lumens as discussed above may be constructed using extrusion, vacuum molding, or another suitable technique.

After step 404, technicians insert the shaping wire 212 into one of the peripheral lumens 210 (step 406). This step may be omitted, however, by constructing the heat transfer extension out of materials having their own shape memory properties, or by using a permanently shaped structure. Whether the shaping wire 212 is used or not, technicians act in step 407 to position the heat transfer extension into the desired coiled shape. The heat transfer extension may be held in such form by means of a metal forming wire, scaffolding, or other positioning structure.

Figure 5:
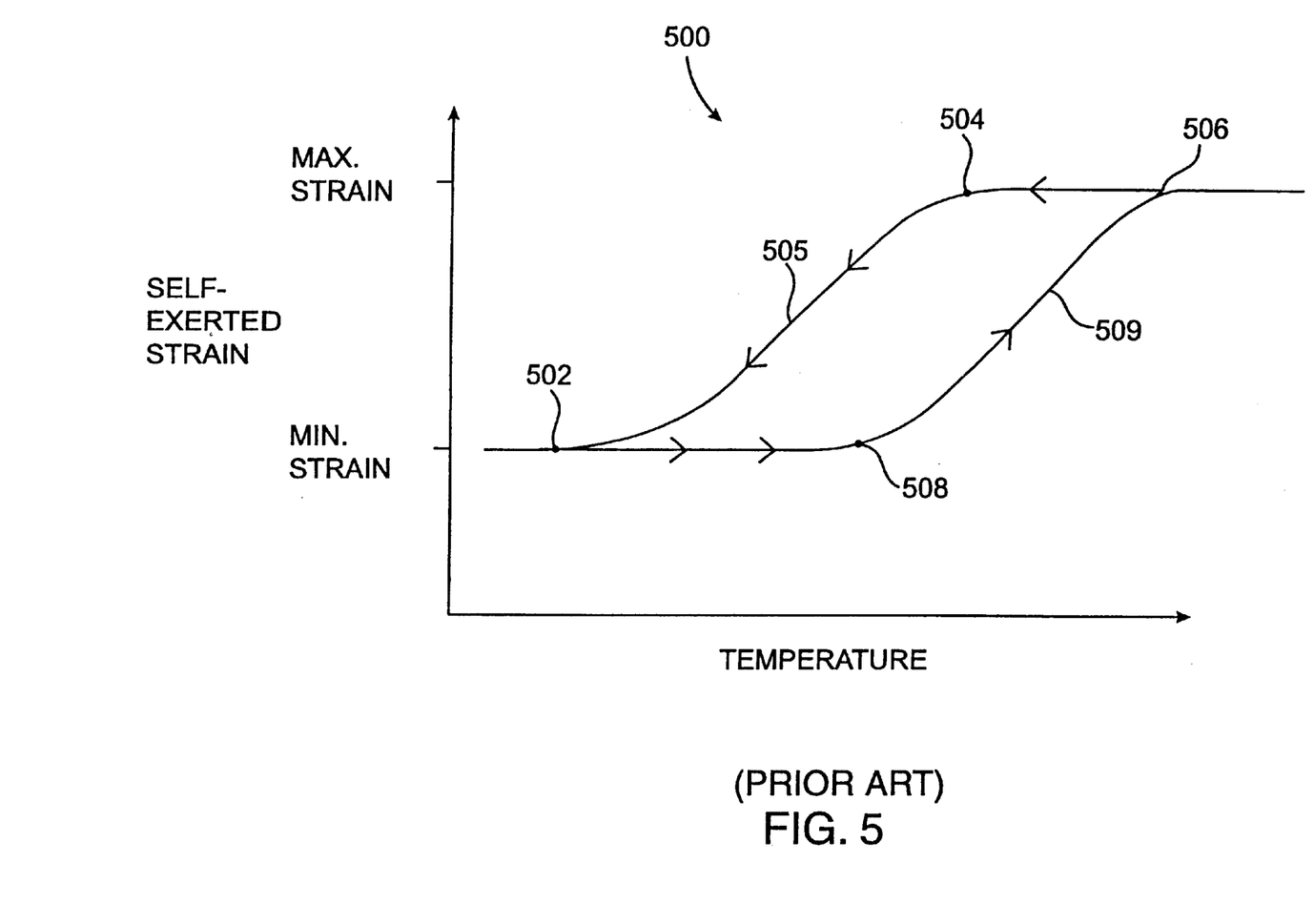
FIG. 5 is a diagram showing the self exerted strain properties of shape memory material over a range of temperatures.

After step 406, the heat transfer extension is placed into an oven (step 408) and heated. Heating is conducted in order to introduce shape memory into the shaping wire 212 and/or the heat transfer extension itself, or to permanently shape the heat transfer extension, depending upon the properties of the materials used. In the case of shape memory materials (e.g., shaping wire 212 or heat transfer extension substance), the heating of step 408 is conducted according to FIG. 5. Referring to FIG. 5, the heat transfer extension's initial temperature is indicated at 502, or less. At this point, the extension has little or no self-exerted strain. As more heat is applied, the extension reaches a temperature indicated at 508. At this temperature 508, shape memory begins to be instilled in the heat transfer extension's shape memory structure (i.e., the wire or the built-in shape memory materials). With greater temperatures, a greater level of self-exerted strain is introduced into the extension, as shown by the temperature/strain path indicated at 509. Finally, upon arriving at a desired temperature 506, the oven is operated to hold a steady temperature. This temperature 506 may, for example, be the temperature providing maximum self-exerted strain. This temperature varies according to the material.

After maintaining the temperature indicated at 506 for a sufficient time, such as one hour, the heat transfer extension is cooled. One exemplary cooling technique involves immersing the extension in cold water. The extension is immersed until it cools sufficiently for the materials to adopt, as a default shape, the coiled shape held during heating. During cooling, the temperature of the heat transfer extension subsides along a path 505, ultimately returning (and optionally passing) the initial temperature 502. Upon reaching the temperature 502, the shape-memory-equipped heat transfer extension once again has minimal self-exerted strain.

After the heat transfer extension has been heated and cooled in steps 408, 410 to introduce shape memory, temperatures at and beneath the point 502 are considered "shape-relaxed," since they induce minimal self-exerted strain in the heat transfer extension. In contrast, temperatures above this point are "shape-active," since they cause the heat transfer extension to assume the form held during original oven heating. Past the temperature 502, even greater temperatures induce proportionally greater self-exerted strain in the heat transfer extension.

As an alternative to steps 408, 410, where materials of the heat transfer extension are susceptible to permanent shaping rather than shape memory, step 408 merely heats the material beyond a fixing temperature, then step 410 cools the material to permanently retain its coiled shape. As a further alternative, steps 408, 410 may introduce a combination of strong or weak permanent shaping (e.g., the tube material itself) as desired, along with temperature-dependent shaping (e.g., the shaping wire 212).

After step 410, technicians in step 412 remove the metal forming wire or other temporary forming structure used to hold the shape of the extension 102 (as installed by step 407). Then, the newly shaped heat transfer extension is assimilated with the other components of the catheter 100, such as the pump interface 106, fluid transfer housing 105, and the like (step 414). After step 414, the sequence 400 ends in step 416.

Using the Catheter

Figure 6:
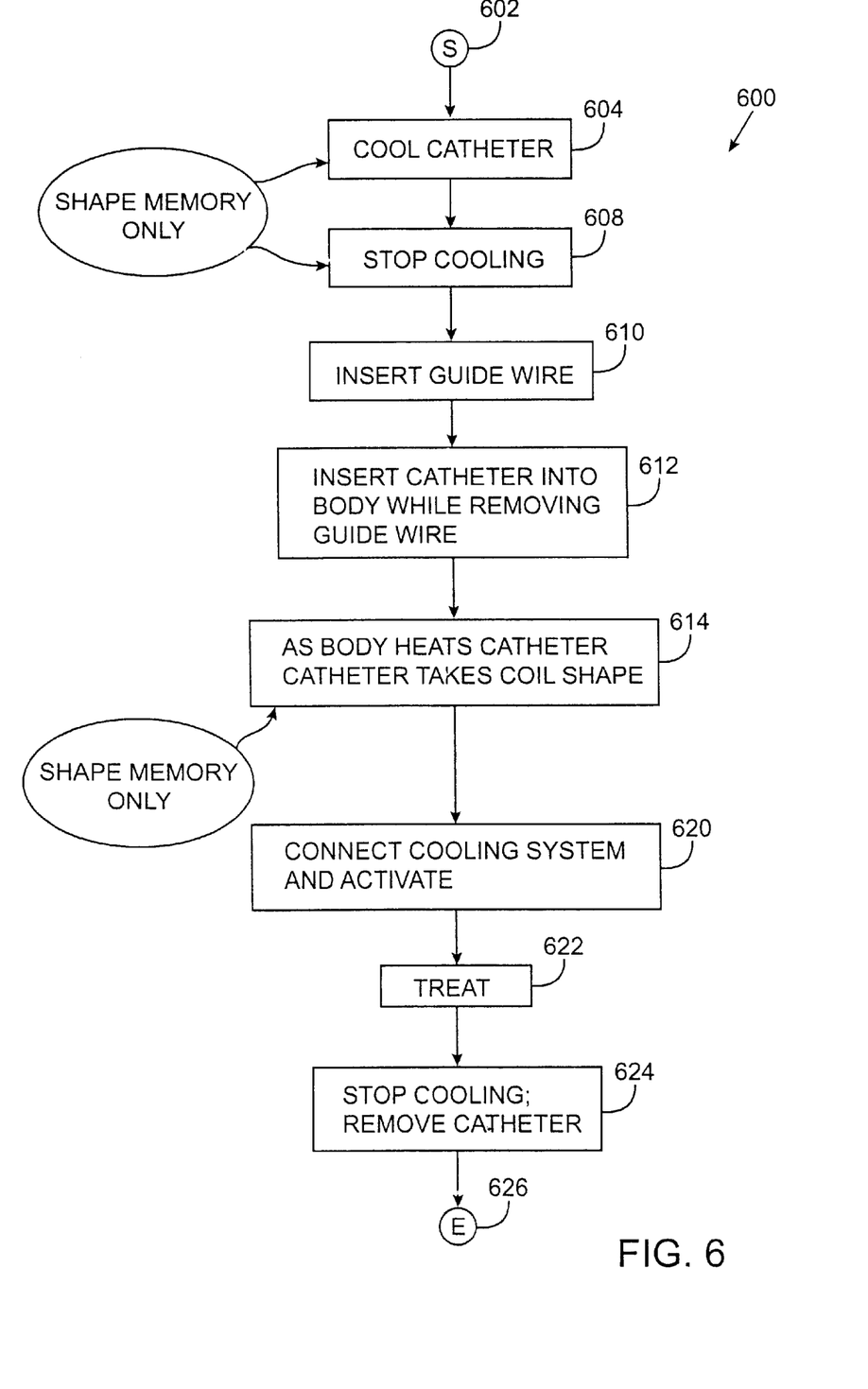
FIG. 6 is a flowchart of an operational sequence for using the catheter of FIG. 1 with a patient, in accordance with the invention.

FIG. 6 illustrates a sequence of exemplary operations 600 for utilizing a catheter of this invention to treat a patient. For ease of explanation, but without any intended limitation, the example of FIG. 6 is described in the specific context of the catheter 100 (FIG. 1) described above. Prior to the steps 600, physicians prepare the patient (not shown) for treatment. This may involve cleaning and disinfecting skin, removing hair, administering medicine, and other known procedures to ready the patient for surgery or other treatment. Also prior to the steps 600, physicians prepare an existing body opening or create a new opening for insertion of the catheter 100. As an example of creating a new opening, doctors may cut an appropriately located incision or puncture for insertion of the catheter into the interior vena cava, using the Seldinger technique.

Step 602 marks the beginning of the sequence 600. Steps 604, 608 are only performed for catheters with a shape-memory-equipped heat transfer extension, e.g., shaping wire 212 or built-in shape memory. In step 604, the shape-memory catheter 100 is cooled to its shape-relaxed temperature range. Namely, while the catheter 100 is outside the body, physicians attach the pump interface 106 to a coolant source and circulate coolant to/from the catheter 100. The coolant source may comprise, for example, a syringe, mechanized pump, hand pump, gravity feed system, or another appropriate device for circulating a coolant fluid through the catheter 100. Coolant is supplied at the coolant supply connector 108, and flows down the pump interface 106. Due to positive pressure upon coolant arriving from the supply connector 108, the coolant passes from the passageway 323 of the pump interface 106 through the fluid transfer housing 105, where it is routed into the supply lumens of the extension 102. The coolant then travels through the supply lumens to the distal reservoir 250. The distal reservoir 250 redirects supply fluid into opposite direction travel down the return lumen. Then, the housing 105 directs fluid from the return lumen into the return line 322 inside the interface 106, and ultimately to the coolant return port 110. Of course, the opposite direction fluid path may be used instead, without departing from the scope of this invention. When the catheter 100 is cooled sufficiently, physicians stop the cooling of step 608.

After steps 604, 608 are performed (shape memory embodiments only), physicians insert a guide wire (not shown) into the catheter 100 (step 610). For this operation, the pump interface 106 is removed from the catheter 100, leaving the catheter's proximal end open. Insertion of the guide wire has the effect of initially straightening the coils of a permanently shaped heat transfer extension, or further straightening the coils of a shape-memory-equipped heat transfer extension (which are already somewhat straight due to the shape relaxed state induced by the cooling of step 604). The guide wire is different than the shaping wire 212, which resides inside the catheter 100 at all times. The use of guide wires for inserting catheters is well known in the art. With the guide wire in place, the operation of inserting the catheter into the patient begins (step 612). The distal tip of the catheter 100 is slid into the opening in the patient's body. If desired, the catheter may be inserted through an introducer sheath (not shown), nozzle, tube, funnel, or another device designed to ease catheter insertion. The catheter 100 and guide wire are slidably moved into the patient's body. During this process, the guide wire protrudes out of the proximal end of the housing 105. Next, while moving the catheter 100 further into the patient's body, physicians begin to simultaneously remove the guide wire in proportion to the inward movement of the catheter.

Insertion of the catheter and removal of the guide wire continues until the guide wire is completely removed, and the catheter resides at its desired position. This completes step 612. As an alternative to the foregoing embodiment of step 612, the catheter may be inserted "over the wire." As mentioned above, the "over the wire" catheter includes a distal valve 275 to selectively admit the guide wire into one of the lumens, and automatically re-seal itself when the wire is removed. in this embodiment, step 612 is performed by inserting the guide wire into the body first, and then sliding the catheter's distal end upon the guide wire's proximal end; the guide wire's proximal end proceeds into the catheter via the pass-through valve 275. With guidance from the "over the wire" guide wire, the catheter is slidably moved into the desired position in the patient's body, and the guide wire is withdrawn.

After completion of step 612, whether "over the wire" or not, removal of the guide wire permits a permanently shaped heat transfer extension coil into its normal shape right away. In the case of shape memory induced coils, step 614 assists the catheter in reaching its coiled state. Namely, as body heat warms the heat transfer extension, the shape memory material experiences increasing self-induced strain, tending to coil the extension. Next, physicians couple the catheter to the coolant circulating system as discussed above, and begin to circulate the coolant through the catheter (step 620). Coolant circulates through the catheter in the same manner discussed above; as it circulates, the coolant removes body heat because of the supply lumens' thin walls and their substantial surface area that is exposed to the surrounding liquid (e.g., arterial or venous blood, etc.) that immerses the catheter 100. Coolant may be circulated, for example, at the rate of 400 milliliters per minute. Physicians commence surgery or other treatment of the patient (step 622) when the targeted body region reaches a desired temperature. Arrival at this temperature may be recognized by measuring the temperature of a concentrated target region (localized hypothermia), or measuring the body core temperature (systemic hypothermia).

In addition to cooling, the catheter may be used for other purposes during treatment. As mentioned above, certain of the lumens may be configured as flow through lumens for the purpose of exchanging materials with the patient. With this hardware embodiment, treatment of step 622 may also be accompanied by using these lumens for delivering materials such as medicine to the patient, and/or sampling substances such as blood from the patient.

After the treatment of step 622 is complete, physicians stop circulating the coolant and remove the catheter in step 624. Or, depending upon the treatment being performed, physicians may decide to continue operating the catheter for some time after treatment ends. For example, the patient can be re-warmed in a controlled manner after therapeutic hypothermia by using the body core temperature as a feedback signal to cause less-cool or possibly warm (>38° Celsius) saline to flow through the catheter. In re-warming the patient, the system monitors the rate of warm-up rate to avoid re-warming too rapidly or too slowly.

The catheter is removed by re-inserting the guide wire while simultaneously withdrawing the catheter. Insertion of the guide wire is useful to straighten the coils, and thereby configure the catheter for easy removal. As another part of step 624, the patient's incision (if any) is closed and any other applicable post treatment procedures are performed. The sequence ends in step 626.

The treatment technique 600 provides a number of distinct advantages. For example, the heat transfer extension provides a substantial amount of heat exchange because its coiled configuration (in the body) provides a large surface area within a compact volume. Heat exchange is also encouraged because the lumens are few in number, and therefore larger, and also because flow is increased by balancing flow resistance between supply and return lumens. As another benefit, the technique 600 helps minimize blood clotting because of the catheter's design. Namely, the catheter of this invention provides a continuous smooth surface from end to end, thereby avoiding angular junctions, narrow passages, binding components, and other structures that might tend to form blood clots.

OTHER EMBODIMENTS

While the foregoing disclosure shows a number of illustrative embodiments of the invention, it will be apparent to those skilled in the art that various changes and modifications can be made herein without departing from the scope of the invention as defined by the appended claims. Furthermore, although elements of the invention may be described or claimed in the singular, the plural is contemplated unless limitation to the singular is explicitly stated.

Moreover, the present invention is presently described in the context of the human body merely for ease of illustration, without any intended limitation. The invention may also be practiced with other beings, such as mammals, birds, reptiles, or other creatures. Furthermore, although the foregoing discussion has described catheter use to induce a hypothermic state, ordinarily skilled artisans (having the benefit of this disclosure) will recognize that the invention also contemplates the use of catheters to induce systemic or local hyperthermia.

Additionally, although certain fluid flow paths have been specifically illustrated for ease of understanding, opposite direction flow paths may be used instead. In such alternatives, references to "supply" or "return" lines or ends are accordingly reversed.

What is claimed is:

1. A catheter, comprising:
    an elongate heat transfer extension housing having at least one supply lumen and at least on return lumen running longitudinally along the extension, the extension also including a distal fluid exchange reservoir providing a fluid redirecting path between the supply and return lumens;
    a shape memory alloy structure causing the heat transfer extension to assume a coiled shape under predetermined shape-active temperatures and a non-coiled shape under predetermined shape-relaxed temperatures different from the shape-active temperatures; and
    the lumens comprising a central lumen surrounded by multiple peripheral lumens,
    wherein the central lumen is the return lumen and the peripheral lumens are the supply lumens.

2. A catheter, comprising:
    an elongate heat transfer extension housing having at least one supply lumen and at least on return lumen running longitudinally along the extension, the extension also including a distal fluid exchange reservoir providing a fluid redirecting path between the supply and return lumens;
    a shape memory alloy structure causing the heat transfer extension to assume a coiled shape under predetermined shape-active temperatures and a non-coiled shape under predetermined shape-relaxed temperatures different from the shape-active temperatures; and
    a shaping wire residing in one of the lumens and running longitudinally along the extension, the shaping wire comprising a material with a shape memory causing the wire to assume a coiled shape under the shape-active temperatures and a non-coiled shape under the shape-relaxed temperatures.

3. The catheter of claim 2, the wire residing in a distal region of the heat transfer extension such that, under the shape-active temperatures, the wire forms a coiled distal region while leaving a substantially straight proximal region.

4. A catheter, comprising;
    an elongate heat transfer extension housing having at least one supply lumen and at least on return lumen running longitudinally along the extension, the extension also including a distal fluid exchange reservoir providing a fluid redirecting path between the supply and return lumens;
    a shape memory alloy structure causing the heat transfer extension to assume a coiled shape under predetermined shape-active temperatures and a non-coiled shape under predetermined shape-relaxed temperatures different from the shape-active temperatures; and
    a valve positioned at the extension, the valve comprising an elastic disk shape member having an aperture penetrating through the disk.

5. A method of operating a heat exchange catheter that includes an elongate heat transfer extension housing at least one supply lumen and at least one return lumen running longitudinally along the extension, the extension also including a distal fluid exchange reservoir providing a fluid redirecting path between the supply and return lumens; shape memory structure causing the heat transfer extension to assume a coiled shape under predetermined shape-active temperatures and a non-coiled shape under predetermined shape-relaxed temperatures different from the shape-active temperatures; the method comprising operations of:
    inserting the catheter into a patient's body;
    responsive to heat of the patient's body, the shape memory structure causing the heat transfer extension to assume the coiled shape; and
    circulating a heat exchange fluid through the catheter.

6. The method of claim 5, where the lumens further include a flow-through lumen and the heat transfer extension includes a barrier separating the flow-through lumen from the fluid exchange reservoir, and the heat transfer extension additionally defines an opening in the flow-through lumen to an exterior of the catheter, and the operations further comprise, after inserting the catheter into the patient's body, exchanging a predetermined substance with the patient's body via the flow-through lumen.

7. The method of claim 6, the exchanging of the predetermined substance comprising delivering the substance to the patient via the flow-through lumen.

8. The method of claim 6, the exchanging of the predetermined substance comprising withdrawing fluid from the patient via the flow-through lumen.

9. The method of claim 5, the operation of inserting the catheter into the patient's body being performed by sliding the catheter over a guide wire.

10. The method of claim 5, the lumens comprising a central lumen surrounded by multiple peripheral lumens, the operation of circulating a heat exchange fluid through the catheter comprising:

circulating fluid outward through the peripheral lumens to the distal tip and then in a reverse direction through the central lumen.

* * * * *

UNITED STATES PATENT AND TRADEMARK OFFICE
CERTIFICATE OF CORRECTION

PATENT NO.    : 6,287,326 B1
DATED         : September 11, 2001
INVENTOR(S)   : Pecor It is certified that error appears in the above-identified patent and that said Letters Patent is hereby corrected as shown below:

Column 11,
Line 56, replace "on" with -- one --.

Column 12,
Line 5, replace "on" with -- one --.
Line 27, replace "on" with -- one --.

Signed and Sealed this

Thirtieth Day of April, 2002

Attest:

Attesting Officer

JAMES E. ROGAN
Director of the United States Patent and Trademark Office